United States Patent [19]

Sakakibara et al.

[11] 4,345,069
[45] Aug. 17, 1982

[54] DEFORMYLTYLOSIN DERIVATIVES

[75] Inventors: Hideo Sakakibara, Mishima; Tatsuro Fujiwara; Osamu Okegawa, both of Shizuoka; Eiichi Honda, Mishima; Susumu Watanabe; Tetsuo Matsuda, both of Shizuoka, all of Japan

[73] Assignee: Toyo Jozo Kabushiki Kaisha, Shizuoka, Japan

[21] Appl. No.: 184,375

[22] Filed: Sep. 5, 1980

[30] Foreign Application Priority Data

Sep. 19, 1979 [JP] Japan .................................. 54-120269
Nov. 13, 1979 [JP] Japan .................................. 54-146642

[51] Int. Cl.³ .......................................... C07H 17/08
[52] U.S. Cl. .................................................. 536/7.1
[58] Field of Search ............. 536/9, 17 R, 17 A, 17 C

[56] References Cited

U.S. PATENT DOCUMENTS 3,321,368 5/1967 Whaley et al. ...................... 424/120
3,769,273 10/1973 Massey .............................. 536/17 R

OTHER PUBLICATIONS

"Antimicrobial Agents and Chemotherapy—1963"--Proceedings of the 3rd Interscience Conference on Antimicrobial Agents & Chemotherapy, Wash. D.C., Oct. 28-30, 1963; Editor J. C. Sylvester-American Society for Microbiology, pp. 45-48.
Tylosin, a New Antibiotic: II. Isolation, Properties, and Preparation of Desmycosin, a Microbiologically Active Degradation Product; Authors–Robert L. Hamill et al., "Antibiotics and Chemotherapy", May 1961, vol. XI, No. 5, pp. 328-335.

Primary Examiner—Blondel Hazel
Attorney, Agent, or Firm—Young & Thompson

[57] ABSTRACT

Deformyltylosin derivatives of the formula

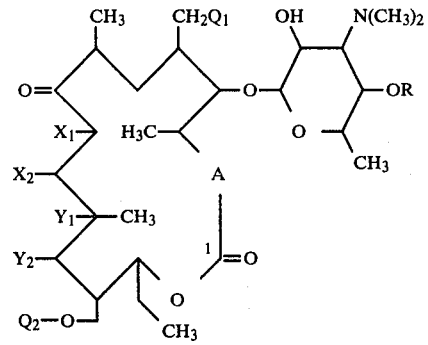

wherein A is

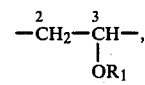

—CH=CH— or —CH$_2$—CH$_2$—, R$_1$ is hydrogen, lower alkanoyl or aryl-lower alkanoyl, X$_1$ and X$_2$ are hydrogen or are connected to form a valence bond, Y$_1$ and Y$_2$ are hydrogen or are connected to form a valence bond, Q$_1$ is hydrogen or methyl, Q$_2$ is hydrogen or

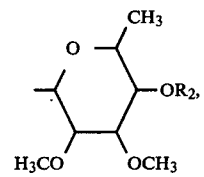

R$_2$ is hydrogen or lower alkanoyl, R is hydrogen or

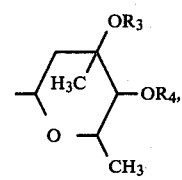

R$_3$ is hydrogen or C$_{2-5}$ alkanoyl, and R$_4$ is hydrogen or C$_{2-6}$ alkanoyl, and when R$_3$ is not hydrogen, then R$_4$ is not hydrogen, or a pharmaceutically acceptable salt thereof, have strong antibacterial activities as compared to the known antibiotic tylosin, and also have enhanced antibacterial activities against all macrolide antibiotic-resistant strains such as A, B and C group strains, and have higher blood levels as compared with tylosin.

27 Claims, No Drawings

DEFORMYLTYLOSIN DERIVATIVES

This invention relates to novel deformyltylosin derivatives. More particularly this invention relates to compounds of the formula

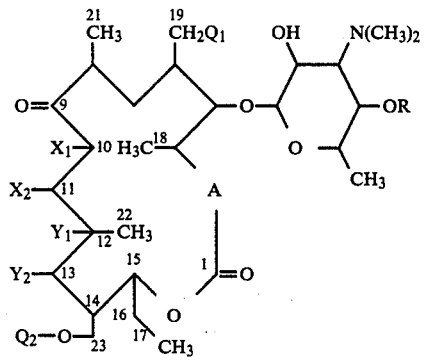

wherein A is

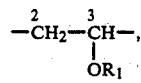

—CH=CH— or —CH$_2$—CH$_2$—, R$_1$ is hydrogen, lower alkanoyl or aryl lower alkanoyl, X$_1$ and X$_2$ each represent hydrogen or are connected to form a valence bond, Y$_1$ and Y$_2$ are connected to form a valence bond or each represent hydrogen, Q$_1$ is hydrogen or methyl, Q$_2$ is hydrogen or

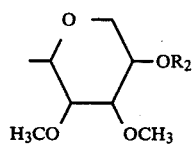

R$_2$ is hydrogen or lower alkanoyl, R is hydrogen or

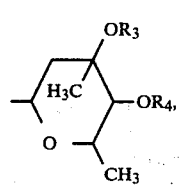

R$_3$ is hydrogen or C$_{2-5}$ alkanoyl, R$_4$ is hydrogen or C$_{2-6}$ alkanoyl, but when R$_3$ is not hydrogen, then R$_4$ is not hydrogen, or a pharmaceutically acceptable salt thereof.

Preferred examples of the salt are inorganic salts such as hydrochloride, sulfate or phosphate, or organic salts such as acetate, propionate, tartrate, citrate, succinate, malate, aspartate or glutamate. Other non-toxic salts are also included.

The novel compounds [1] have strong antibacterial activities as compared to the known antibiotic tylosin, and also have enhanced antibacterial activities against all macrolide antibiotic-resistant strains such as macrolide-resistant A group strains (clinical isolates of etythromycin, oleandomycin and 16-membered macrolide antibiotic-resistant strains), B group strains and C group strains. Especially the said novel compounds have higher blood levels as compared with known tylosin.

The antibiotics [1] of the present invention will be expected to show an excellent clinical infectious therapeutic effect. Furthermore, the present antibiotics are useful for veterinary use or feed additives.

In the course of studying novel derivatives of 16-membered antibiotics, we have found that deformyltylosin or its derivatives prepared by deformylation of tylosin or its derivatives using [(C$_6$H$_5$)$_3$P]$_3$RhCl have strong antibacterial activity as compared with tylosin, and moreover show superior antibacterial activity against macrolide antibiotic-resistant strains, and further show higher blood levels. We have also found that compounds showing such activities can be derived from macrolide antibiotics having the structure of

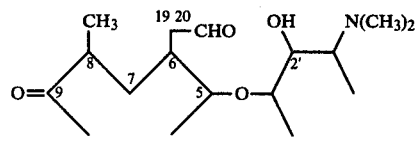

thereby to complete the present invention.

The compound [1] of the present invention can be produced by the following processes:

Process A:

A compound wherein A is

—CH$_2$—CH—,
  |
  OH

X$_1$ and X$_2$ are connected to form a valence bond, Y$_1$ and Y$_2$ are connected to form a valence bond, Q$_1$ is hydrogen, Q$_2$ is mysinosyl, R is mycarosyl, i.e. 19-deformyltylosin of the formula

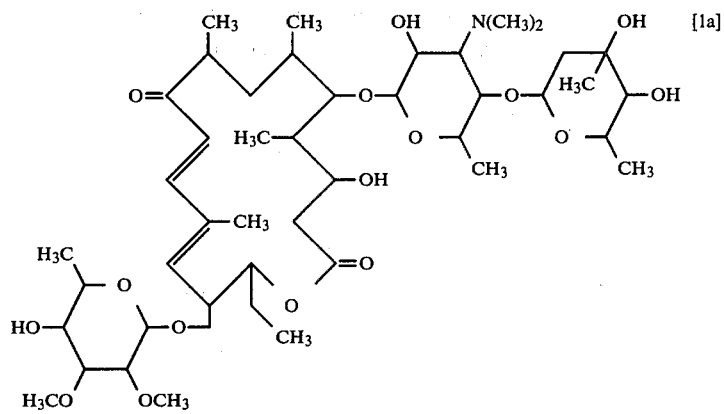

is produced by the following method:

Tylosin is deformylated by chloro-tris (triphenylphosphine) rhodium; [(C$_6$H$_5$)$_3$P]$_3$RhCl in an inert organic solvent under heating.

The preferred example of inert organic solvent is benzene. Heating is performed with reflux. The reaction progress can be checked by silica gel thin layer chromatography and the reaction is terminated upon the disappearance of the starting material tylosin in the reaction mixture.

The product [1a] can be obtained from the reaction mixture by extracting with dilute acid such as dilute hydrochloric acid, adjusting the pH of the extract to pH 9–10 by adding aqueous alkali such as aqueous ammonia, then extracting with a water-immiscible organic solvent such as chloroform and evaporating off the solvent. Further purification is performed by any conventional isolation and purification procedure for macrolide antibiotics for example by chromatography such as on silica gel, active alumina or an adsorption resin.

Process B:

A compound wherein A is

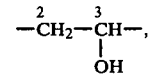

$X_1$ and $X_2$ are connected to form a valence bond, $Y_1$ and $Y_2$ are connected to form a valence bond, $Q_1$ is hydrogen, $Q_2$ is mysinosyl and R is

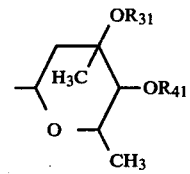

in which $R_{31}$ is $C_{2-5}$ alkanoyl and $R_{41}$ is $C_{2-6}$ alkanoyl, i.e. a compound of the formula

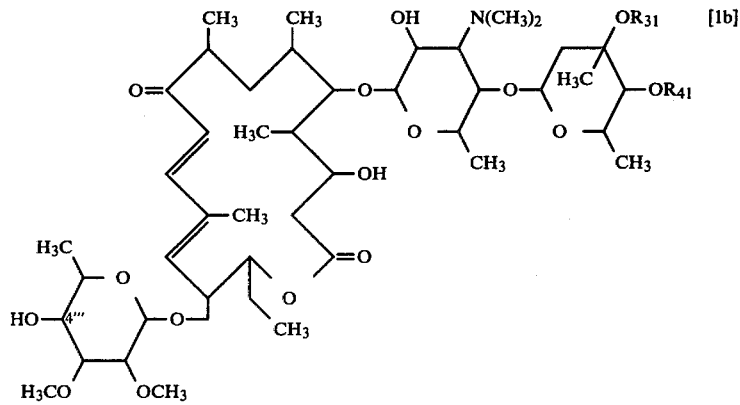

wherein $R_{31}$ and $R_{41}$ have the same meanings hereinabove, is prepared by reacting tylosin, or tylosin with the 4'''-hydroxyl group protected, with aliphatic carboxylic acid anhydride in the presence of inorganic base to obtain a compound of the formula

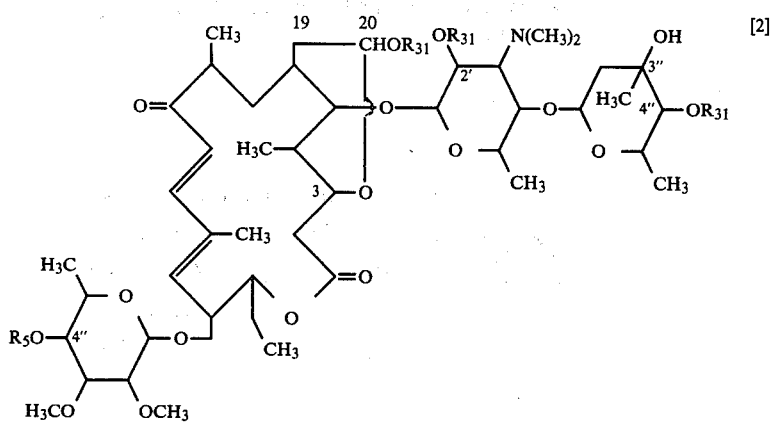

wherein $R_5$ is lower alkanoyl or halo-lower alkanoyl and $R_{31}$ is $C_{2-5}$ alkanoyl, and reacting compound [2] with an aliphatic carboxylic acid anhydride in the presence of tertiary organic amine in an inert organic solvent with heating to prepare a compound of the formula

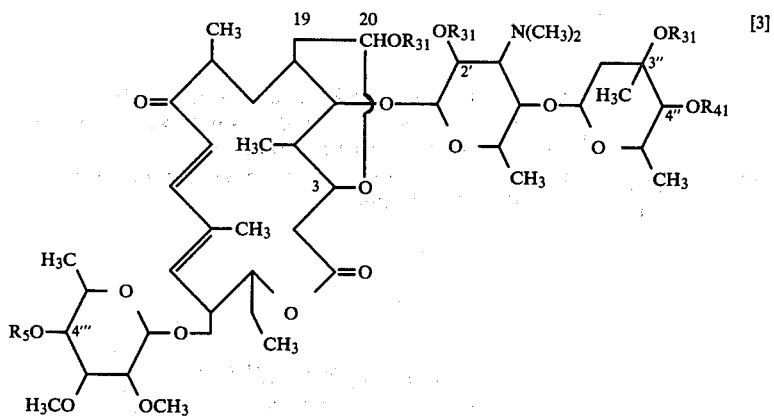

wherein $R_{41}$ is $C_{2-6}$ alkanoyl and $R_{31}$ and $R_5$ have the same meanings hereinabove, and treating the compound [3] with a methanol or ethanol solution of ammonia to remove the protective groups at positions -3, -20 and -4''', then removing the protective group at position-2' by treatment in methanol under heating to obtain a compound of the formula

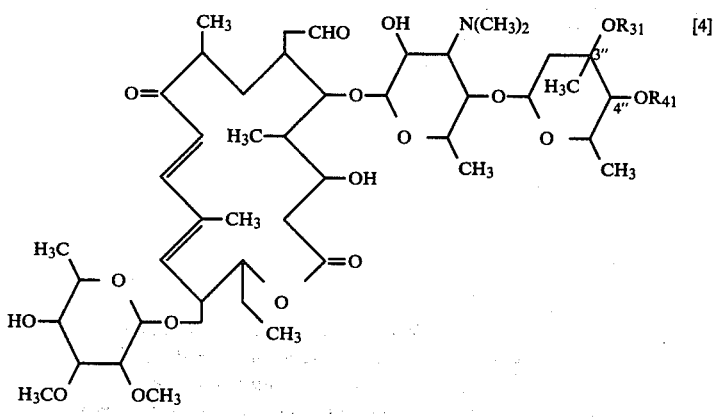

wherein $R_{31}$ and $R_{41}$ have the same meanings hereinbefore, then subjecting the compound [4] to deformylation using $[(C_6H_5)_3P]_3RhCl$ in an inert organic solvent under heating.

Compound [4] is prepared from tylosin, or tylosin with the 4'''-hydroxyl group protected, by the method described in U.S. patent application Ser. No. 75,661, filed Sept. 14, 1979, or British Patent Publication No. 2,031,418 A.

Process C:

A compound wherein A is in which $R_{41}$ is $C_{2-6}$ alkanoyl, i.e. a compound [1c] of the formula

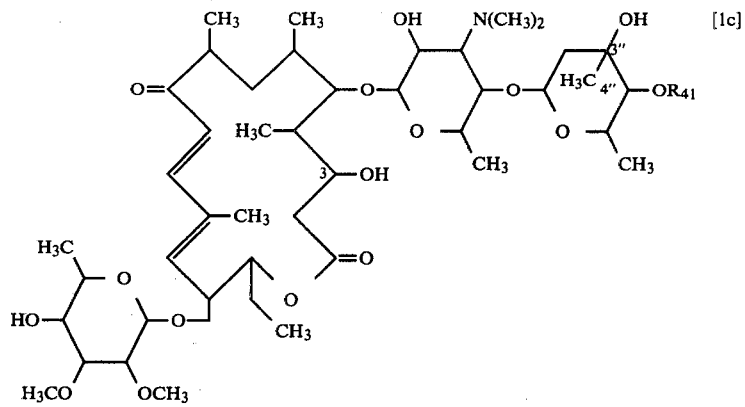

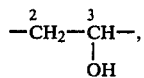

$X_1$ and $X_2$ are connected to form a valence bond, $Y_1$ and $Y_2$ are connected to form a valence bond, $Q_1$ is hydrogen, $Q_2$ is mysinosyl and R is

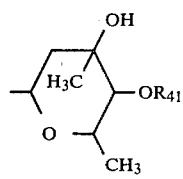

wherein $R_{41}$ is $C_{2-6}$ alkanoyl, is produced by reacting tylosin, or tylosin with the 4'''-hydroxyl group protected, with an aliphatic carboxylic acid anhydride in the presence of an inorganic base to prepare a compound of the formula

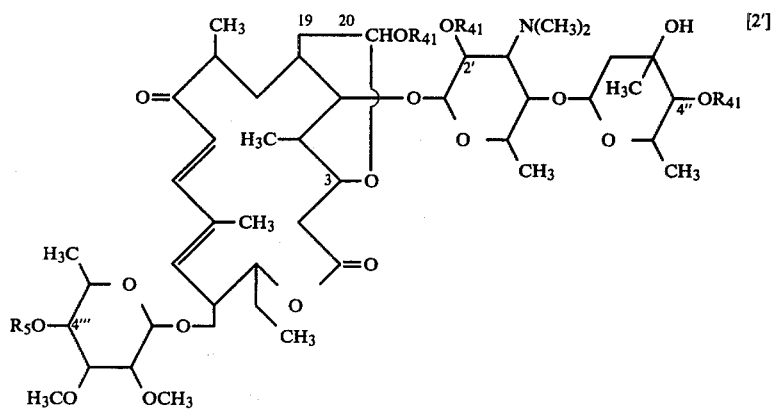

wherein $R_5$ is lower alkanoyl or halo-lower alkanoyl and $R_{41}$ has the same meaning hereinbefore, and treating the compound [2'] with a methanol or ethanol solution of ammonia to remove the protective groups at positions -3, -20 and -4''', then removing the protective group at position 2' by treatment in methanol with heating to obtain a compound of the formula

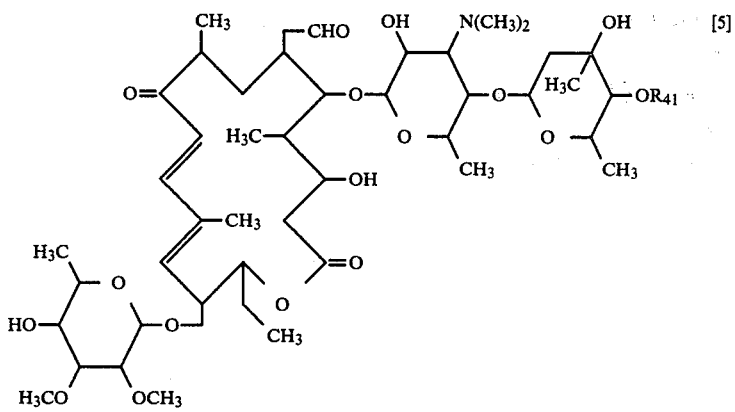

wherein $R_{41}$ has the same meaning hereinbefore, and deformylating the compound [5] with $[(C_6H_5)_3P]_3RhCl$ in an inert organic solvent with heating.

Process D:
A compound wherein A is

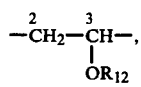

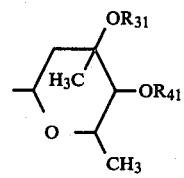

in which $R_{31}$ is $C_{2-5}$ alkanoyl and $R_{41}$ is $C_{2-6}$ alkanoyl, i.e. a compound of the formula

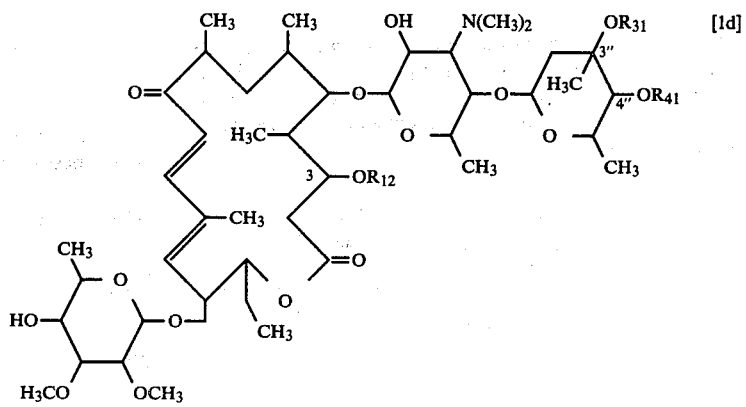

wherein $R_{12}, R_{31}$ and $R_{41}$ have the same meanings hereinbefore.

The compound [1d] is produced as follows:
A compound in which the 2'- or 4'''-hydroxyl group may optionally be protected, of the formula $R_{12}$ is lower alkanoyl, $X_1$ and $X_2$ are connected to form a valence bond, $Y_1$ and $Y_2$ are connected to form a valence bond, $Q_1$ is hydrogen, $Q_2$ is mysinosyl and R is

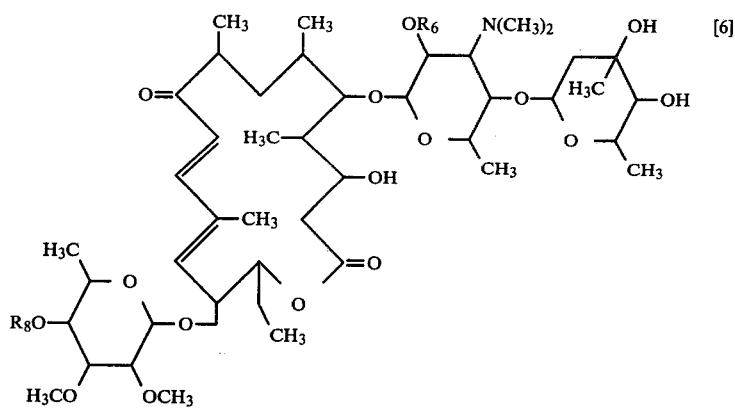

wherein $R_6$ is hydrogen or $R_{61}$, $R_{61}$ is lower alkanoyl, $R_8$ is hydrogen or $R_5$, $R_5$ is lower alkanoyl or halo-lower alkanoyl, is acylated with an aliphatic carboxylic acid halide in the presence of a tertiary organic amine in an inert organic solvent to obtain a compound of the formula

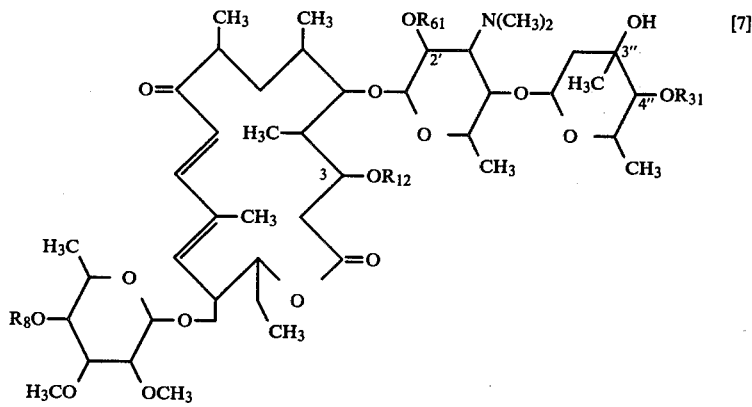

wherein $R_{12}$, $R_{31}$, $R_{61}$ and $R_8$ have the same meanings hereinbefore, then the said compound [7] is acylated with an aliphatic carboxylic acid anhydride in the presence of a base with heating to obtain a compound of the formula

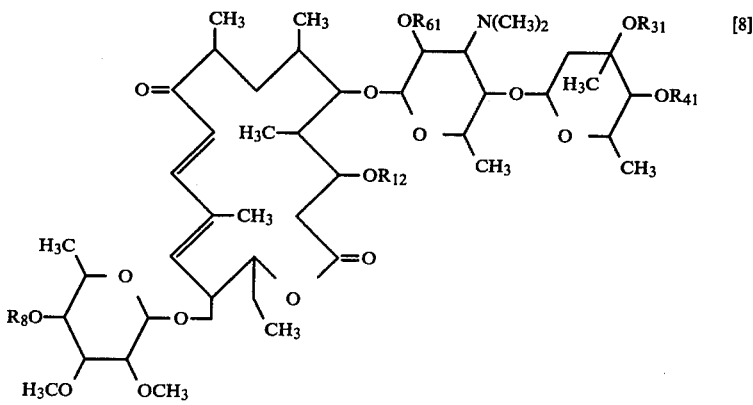

wherein $R_{12}$, $R_{31}$, $R_{41}$, $R_{61}$ and $R_8$ have the same meanings hereinbefore, then the said compound [8] is treated with methanolic or ethanolic ammonia to remove the protective group for position-4''', and the protective group at position-2' is removed by heating in methanol.

Process E:

A compound wherein A is

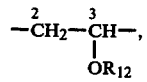

$R_{12}$ is lower alkanoyl, $X_1$ and $X_2$ are connected to form a valence bond, $Y_1$ and $Y_2$ are connected to form a valence bond, $Q_1$ is hydrogen, $Q_2$ is mysinosyl, R is

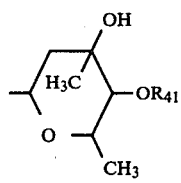

treating with methanol with heating to remove the protective group at position-2'.

A compound [1e] wherein $R_{12}$ and $R_{41}$ are not identical groups can be prepared by treating the compound [2'] with ammonia in methanol or ethanol within a reaction time insufficient to remove the protective group at position-4''', but sufficient to remove the protective groups at positions -3 and -20 to prepare a compound of the formula

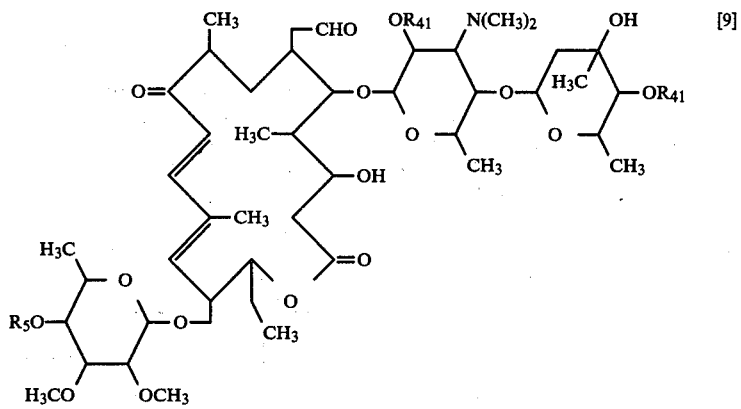

in which $R_{41}$ is $C_{2-6}$ alkanoyl, i.e. a compound of the formula wherein $R_5$ is lower alkanoyl or halo-lower alkanoyl and $R_{41}$ has the same meaning hereinbefore, then acylat-

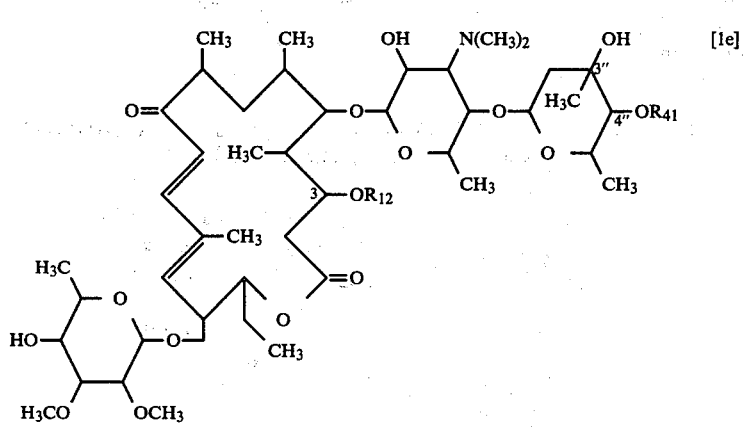

wherein $R_{12}$ and $R_{41}$ have the same meanings hereinbefore, is produced by treating the compound [7'] with ammonia in methanol or ethanol to remove the protective group at position-4''' of the compound [7'] (a compound [D] in the process D wherein $R_{31}$ is $R_{41}$), and ing the said compound [9] with a lower aliphatic carboxylic acid halide in an inert organic solvent in the presence of a tertiary organic amine to obtain a compound of the formula

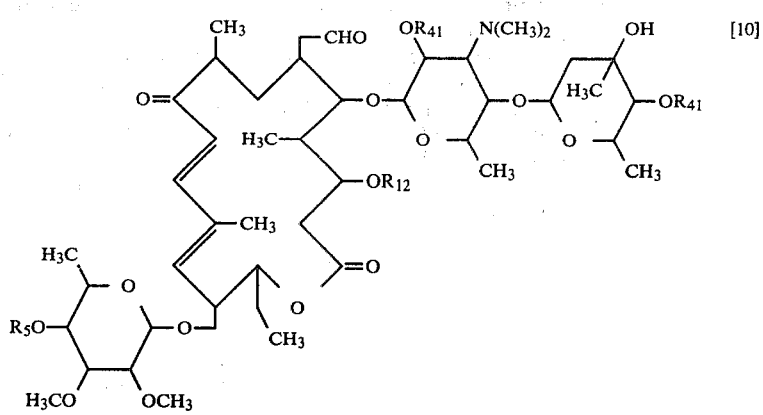

wherein $R_{12}$, $R_{41}$ and $R_5$ have the same meanings hereinbefore, and treating the said compound [10] with ammonia in methanol or ethanol to remove the protective group at position-4''', further treating in methanol with heating to remove the protective group at position-2' to prepare a compound of the formula

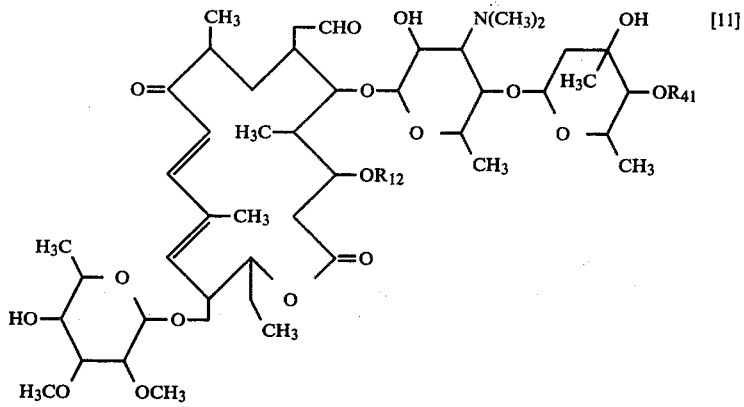

wherein $R_{12}$ and $R_{41}$ have the same meanings hereinbefore, and then deformylating the compound [11] with [(C$_6$H$_5$)$_3$P]$_3$RhCl in an inert organic solvent with heating.

Process F:

A compound wherein A is —CH=CH—, $X_1$ and $X_2$ are connected to form a valence bond, $Y_1$ and $Y_2$ are connected to form a valence bond, Q is mysinosyl, R is

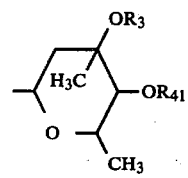

($R_{41}$ is $C_{2-6}$ alkanoyl, $R_3$ is hydrogen or $R_{31}$, $R_{31}$ is $C_{2-6}$ alkanoyl, i.e. a compound of the formula

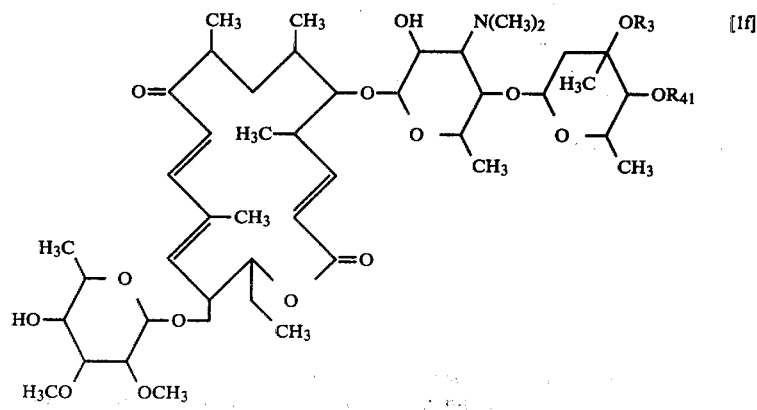

wherein $R_3$ and $R_{41}$ have the same meanings hereinbefore, is prepared by reacting the compound [1d] or [1e]

with an alcolate in alcohol. Examples of alcolate are CH₃ONa, C₂H₅ONa and others. The reaction proceeds at room temperature; however, if the reaction rate is slow, it can be heated, and its end point is marked by disappearance of the compound [1d] or [1e] as detected by silica gel thin layer chromatography.

The compound [1f] can be obtained by the same isolation method as the compound [1a] in process A.

Process G:

A compound wherein A is

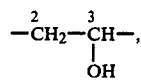

$X_1$ and $X_2$ are connected to form a valence bond, $Y_1$ and $Y_2$ are connected to form a valence bond, $Q_1$ is hydrogen, $Q_2$ is mysinosyl and R is hydrogen, i.e. 19-deformyl-4'-demycarosyltylosin, of the formula

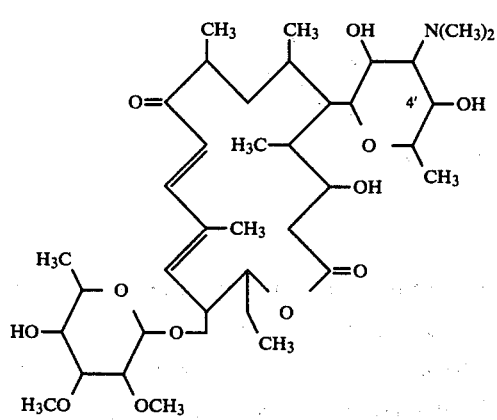

is prepared by deformylating 4'-demycarosyltylosin with [(C₆H₅)₃P]₃RhCl in an inert organic solvent.

4'-demycarosyltylosin can be prepared by hydrochloric acid hydrolysis of tylosin. [Antibiot. and Chemoth., 11, 328 (1961)].

Deformylation of 4'-demycarosyltylosin can be performed by the same process as in process A hereinbefore.

Compound [1g] can be isolated and purified by the same procedures as in process A hereinbefore.

Process H:

A compound wherein A is

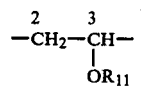

($R_{11}$ is lower alkanoyl or aryl-lower alkanoyl, $X_1$ and $X_2$ are connected to form a valence bond, $Y_1$ and $Y_2$ are connected to form a valence bond, $Q_1$ is hydrogen, $Q_2$ is mysinosyl and R is hydrogen, i.e. a compound of the formula

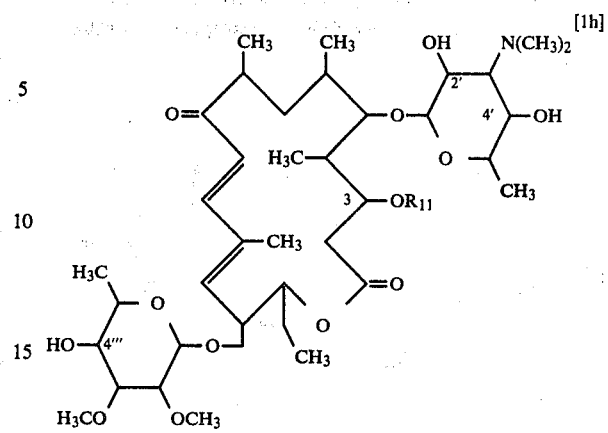

wherein $R_{11}$ has the same meaning hereinbefore, is prepared by reacting 4'-demycarosyltylosin with a lower aliphatic carboxylic acid anhydride in an inert organic solvent to prepare a compound of the formula

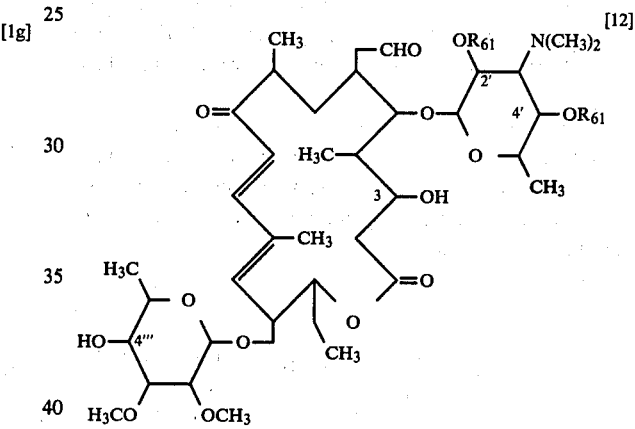

wherein $R_{61}$ is lower alkanoyl, reacting the said compound [12] with a lower aliphatic carboxylic acid halide or an aryl lower aliphatic carboxylic acid halide to prepare a compound of the formula

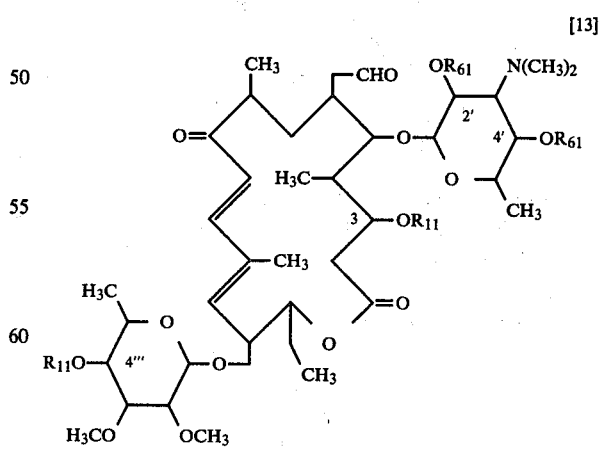

wherein $R_{11}$ and $R_{61}$ have the same meanings hereinbefore, treating the compound [13] in methanol with heating to remove the protective groups at positions -2' and -4', then removing the protective group at position-4'''
in ammonia-saturated methanol to prepare a compound
[14] of the formula

[14]

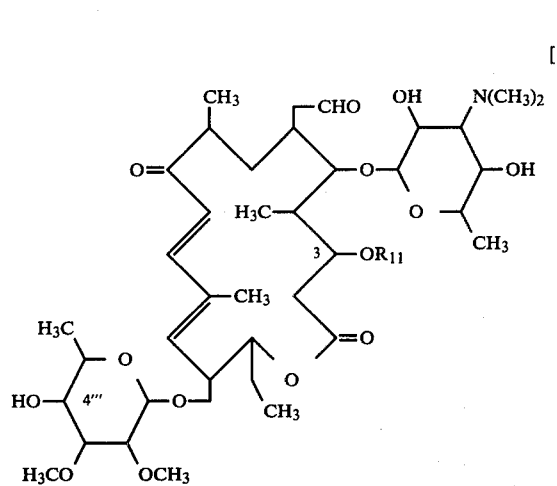

wherein $R_{11}$ has the same meaning hereinbefore, and deformylating the compound [14] with $[(C_6H_5)_3P]_3RhCl$ in an inert organic solvent with heating.

Alternatively, compound [14] can be prepared by reacting 4'-demycarosyltylosin with a lower aliphatic carboxylic acid halide in an inert organic solvent in the presence of a tertiary organic amine to prepare a compound of the formula

[15]

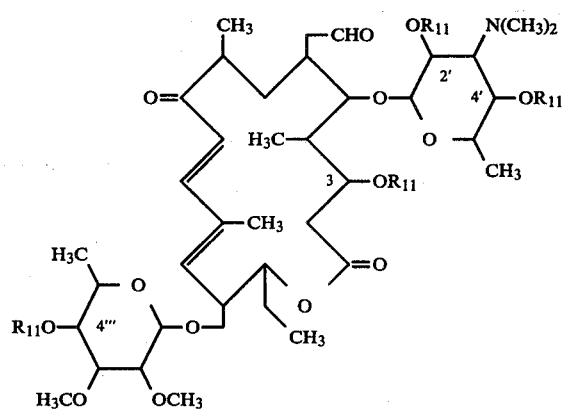

wherein $R_{11}$ has the same meaning hereinbefore, then treating compound [15] by the same procedure as in the case of compound [13].

Process I:

A compound wherein A is

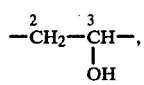

$X_1$ and $X_2$ are connected to form a valence bond, $Y_1$ and $Y_2$ are connected to form a valence bond, $Q_1$ is hydrogen, $Q_2$ is

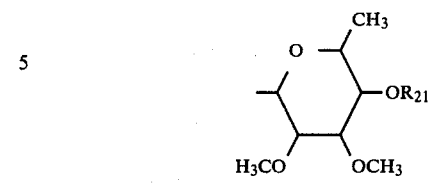

($R_{21}$ is lower alkanoyl) and R is hydrogen, i.e. a compound of the formula

[1i]

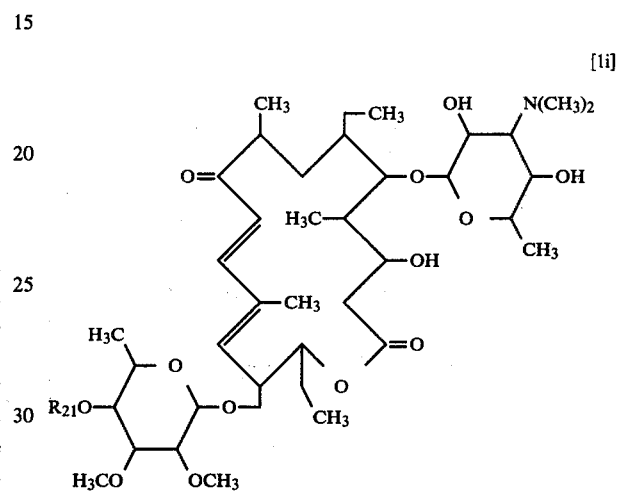

wherein $R_{21}$ has the same meaning hereinbefore, is prepared by reacting compound [12] with a lower aliphatic carboxylic acid halide in an inert organic solvent in the presence of a tertiary organic amine to prepare a compound of the formula

[16]

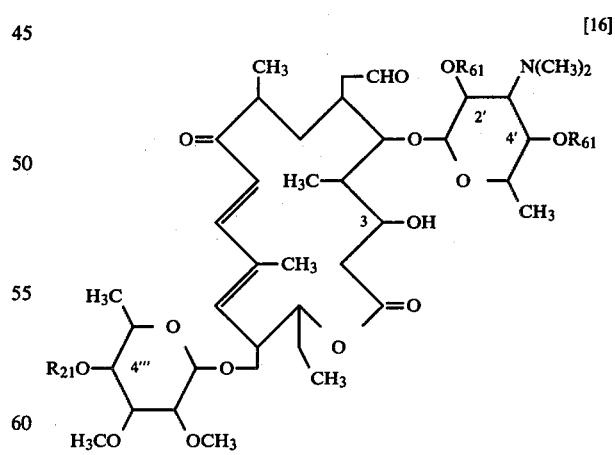

wherein $R_{21}$ and $R_{61}$ have the same meanings hereinbefore, removing the protective group at positions -2' and -4' by treating with methanol with heating to prepare a compound of the formula

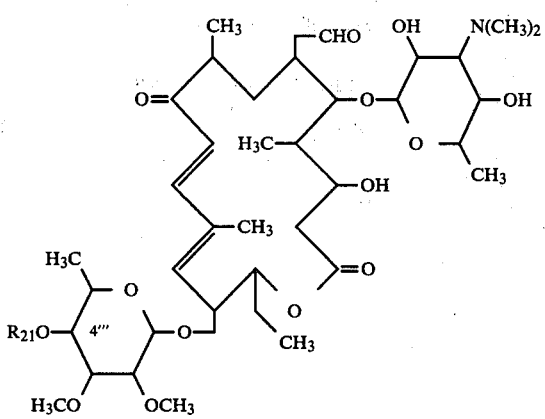

[17]

wherein $R_{21}$ has the same meaning hereinbefore, then deformylating compound [17] with $[(C_6H_5)_3P]_3RhCl$ in an inert organic solvent.

Process J:

A compound wherein A is

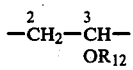

($R_{12}$ is lower alkanoyl), $X_1$ and $X_2$ are connected to form a valence bond, $Y_1$ and $Y_2$ are connected to form a valence bond, $Q_1$ is hydrogen, $Q_2$ is

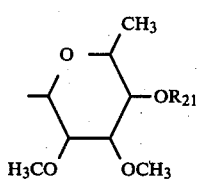

($R_{21}$ is lower alkanoyl) and R is hydrogen, i.e. a compound of the formula

[1j]

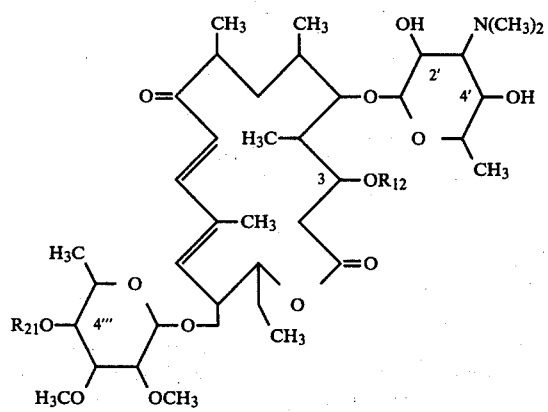

wherein $R_{12}$ and $R_{21}$ have the same meanings hereinbefore, is produced by acylating compound [1g] or compound [1h] in which $R_{11}$ is lower alkanoyl, with a lower aliphatic carboxylic acid anhydride in the presence of a base to prepare a compound of the formula

[18]

wherein $R_{12}$ and $R_{21}$ are lower alkanoyl, then removing the protective groups at positions -2' and -4' in methanol with heating.

Process K:

A compound wherein A is $-CH=CH-$, $X_1$ and $X_2$ are connected to form a valence bond, $Y_1$ and $Y_2$ are connected to form a valence bond, $Q_1$ is hydrogen, $Q_2$ is mysinosyl and R is hydrogen, i.e. 19-deformyl-2,3-didehydro-3-dehydroxy-4'-demycarosyltylosin of the formula

[1k]

is produced by reacting a compound [1h] wherein $R_{11}$ is lower alkanoyl, with an alcolate in an alcoholic solvent. Examples of alcolate are $CH_3ONa$, $C_2H_5ONa$ and others. The reaction proceeds at room temperature; however, heating is effective if the reaction rate is slow. The progress of the reaction can be traced by thin layer chromatography and the end point is indicated by the disappearance of the starting compound [1h].

Isolation of compound [1k] is performed by the same procedures as for the isolation of compound [1a] in process A hereinbefore.

Process L:

A compound wherein A is $$-\overset{2}{C}H_2-\overset{3}{C}H-,$$
$$\quad\quad\quad\quad |$$
$$\quad\quad\quad\quad OH$$

$X_1$, $X_2$, $Y_1$ and $Y_2$ are hydrogen, $Q_1$ is hydrogen, $Q_2$ is mysinosyl and R is hydrogen, i.e. 19-deformyl-4'-demycarosyl-10, 11, 12, 13-tetrahydrotylosin of the formula

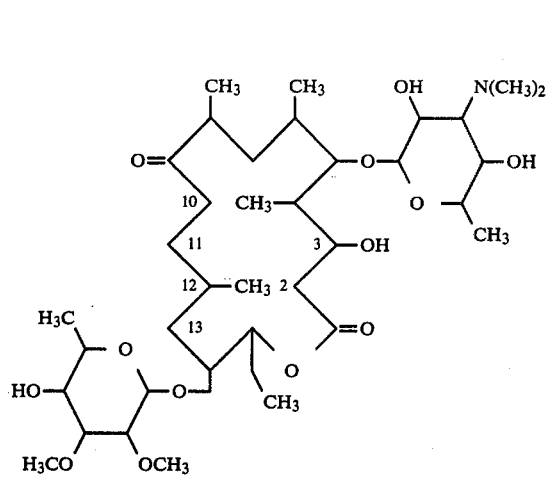

[1l]

is produced by reducing compound [1g].

Compound [1g] is reduced at positions -10, -11, -12 and -13 by catalytic reduction with a heavy metal catalyst such as platinum oxide, palladium carbon or Raney Nickel in methanol or ethanol at room temperature.

The progress of the reaction is traced by thin layer chromatography and the end point is signalled by the disappearance of compound [1g]. Compound [1l] is isolated by drying in vacuo after filtration of the catalyst.

Process M:

A compound wherein A is —CH$_2$—CH$_2$—, $X_1$, $X_2$, $Y_1$, $Y_2$ and $Q_1$ are hydrogen, $Q_2$ is mysinosyl and R is hydrogen, i.e. 19-deformyl-3-dehydroxy-4'-demycarosyl-10, 11, 12, 13-tetrahydrotylosin of the formula

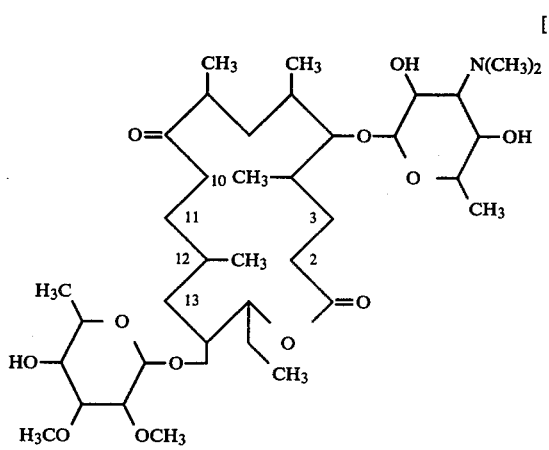

[1m]

is produced by reducing compound [1k]. Reduction of compound [1k] can be performed by the same procedure as in process L hereinabove.

Process N:

A compound wherein A is

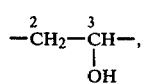

$X_1$ and $X_2$ are connected to form a valence bond, $Y_1$ and $Y_2$ are connected to form a valence bond, and $Q_1$, $Q_2$ and R are hydrogen, i.e. 19-deformyl-4'-demycarosyl-23-demysinosyltylosin of the formula

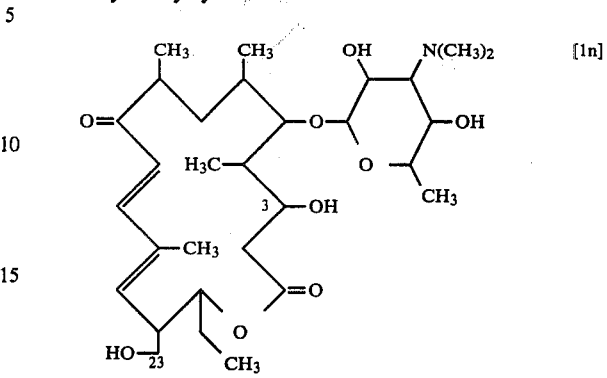

[1n]

is produced by deformylating 4'-demycarosyl-23-demysinosyltylosin with [(C$_6$H$_5$)$_3$P]$_3$RhCl in an inert organic solvent with heating.

4'-demycarosyl-23-demysinosyltylosin is prepared by hydrochloric acid hydrolysis of 4'-demycarosyltylosin [Tetrahedron Letters, 4737 (1970)].

The above deformylation and isolation and purification can be performed by the same procedure as described in process A hereinbefore.

Process O:

A compound wherein A is

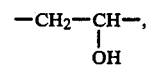

$X_1$ and $X_2$ are connected to form a valence bond, $Y_1$ and $Y_2$ are connected to form a valence bond, $Q_1$ is methyl, $Q_2$ is mysinosyl and R is hydrogen, i.e. 20-deoxo-4'-demycarosyltylosin of the formula

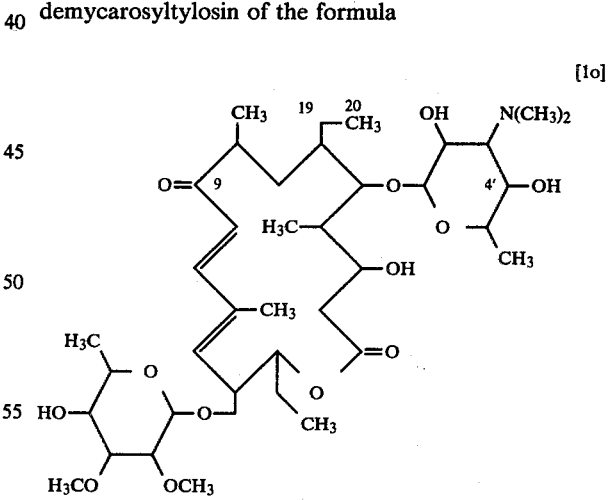

[1o]

is produced by reducing the CHO group at position -19 of tylosin to a CH$_2$OH group, exchanging the CH$_2$OH group to a CH$_3$ group to prepare 20-deoxotylosin, and de-4'-mycarosylating the obtained 20-deoxotylosin with diluted acid.

Alternatively, compound [1o] can be prepared by previous 4'-demycarosylation of tylosin, followed by reduction of the CHO group at position -19 to a CH$_2$OH group.

The minimum inhibitory concentrations of the products are shown in Table 1.

TABLE 1

| | Minimum Inhibitory Concentration (μg/ml) | | | | | | |
|---|---|---|---|---|---|---|---|
| | Compound | | | | | | |
| Test organisms | 19-deformyl-tylosin | 19-deformyl-4'-demycarosyl-tylosin | 19-deformyl-2,3-didehydro-3-dehydroxy-4'-demycarosyltylosin | 19-deformyl-4'-demycarosyl-3-phenylacetyl-tylosin | 20-deoxo-4'-demycarosyltylosin | Control tylosin | Control erythromycin |
| Staphylococcus aureus ATCC 6538p | 1.6 | 0.2 | 0.2 | 0.2 | 0.2 | 1.6 | 0.2 |
| Staphylococcus aureus MS353 | 1.6 | 0.2 | 0.2 | 0.2 | 0.2 | 3.1 | 0.2 |
| Staphylococcus aureus MS353 C36* | 0.8 | 0.2 | 0.4 | 0.1 | 0.1 | 1.6 | >100 |
| Staphylococcus aureus 0126** | | 0.8 | 1.6 | 0.4 | | 1.6 | >100 |
| Streptococcus pyogenes N.Y.5 | 1.6 | 0.1 | 0.2 | ≦0.05 | 0.2 | 0.4 | ≦0.05 |

*erythromycin resistant strain
**erythromycin and oreandomycin resistant strain.

The following examples illustrate the process of the present invention.

The Rf values in the examples are, if not specified, measured by the following carrier and developers:
Carrier: Merck, silica gel 60 Art 5721.
Developer:
A: n-hexane-benzene-acetone-ethyl acetate-methanol (90:80:25:60:30).
B: chloroform-methanol-acetic acid-water (80:7:7:1).

EXAMPLE 1

19-deformyltylosin $[(C_6H_5)_3P]_3RhCl$ (2.1 g) was added to tylosin (1.83 g) dissolved in benzen (50 ml) and the mixture was refluxed for six hours. The reaction mixture was filtered and the filtrate was extracted twice with 0.1 N hydrochloric acid (50 ml). The aqueous layer was adjusted to pH 9 by adding aqueous ammonia and extracted with chloroform (100 ml). The extract was dried with anhydrous magnesium sulfate and dried in vacuo to obtain the product (1.15 g).

TLC: $Rf_A=0.23$, $Rf_B=0.24$.

Mass spectrum (m/e): 887 (M+), 743, 725, 553, 510, 362, 318, 191, 175, 174, 145.

NMR spectrum (100 MHz, CDCl$_3$): disappearance of proton in aldehyde.

EXAMPLE 2

3''-acetyl-19-deformyl-4''-isovaleryltylosin $[(C_6H_5)_3P]_3RhCl$ (1 g) was added to a solution of 3''-acetyl-4''-isovaleryltylosin (1 g) dissolved in benzene (20 ml) and the mixture was refluxed for six hours. The reaction mixture was filtered and the filtrate was dried in vacuo. The residue was purified by silica gel column chromatography using benzene-acetone (7:1) to obtain 3''-acetyl-19-deformyl-4''-isovaleryltylosin (700 mg).

TLC: $Rf_A=0.53$, $Rf_B=0.78$.

Mass spectrum (m/e): 1013 (M+), 912 (M+-101), 362, 271, 211, 191, 190, 175, 174, 173, 169.

NMR spectrum (100 MHz, CDCl$_3$): 1.77 (12-CH$_3$), 2.00 (3''-OAc).

A process for production of the above 3''-acetyl-4''-isovaleryltylosin is described in British Patent Publication No. 2,031,418 A.

EXAMPLE 3

3,3'',4''-triacetyl-19-deformyltylosin and 3'',4''-diacetyl-19-deformyl-2,3-didehydro-3-dehydroxytylosin Acetic anhydride (1.5 ml) was added to a solution of 19-deformyltylosin (950 mg) dissolved in dry pyridine (10 ml) and the mixture was heated at 100° C. for 70 hours. The reaction mixture was concentrated in vacuo and extracted with chloroform (50 ml). The chloroform layer was washed with 0.1 N-HCl, water and diluted aqueous ammonia, dried with anhydrous magnesium sulfate and dried in vacuo. C$_2$H$_5$ONa (70 mg) was added to a solution of the residue dissolved in ethanol (20 ml), and the mixture was stirred for one hour at room temperature and dried in vacuo. The residue was dissolved in methanol saturated with ammonia (20 ml) and stirred for six hours at room temperature. Water (50 ml) was added to the reaction mixture, which was then extracted with chloroform (50 ml). The chloroform layer was dehydrated, dried in vacuo, dissolved in methanol (20 ml) and refluxed for 16 hours. The reaction mixture was dried in vacuo to yield the crude product (1.05 g) which was purified by silica gel column chromatography using benzene-acetone (6:1) to obtain 3,3'',4''-triacetyl-19-deformyltylosin (350 mg) and 3'',4''-diacetyl-19-deformyl-2,3-didehydro-3-dehydroxytylosin (280 mg).

3,3'',4''-triacetyl-19-deformyltylosin:

TLC: $Rf_A=0.52$, $Rf_B=0.77$.

Mass spectrum (m/e): 953 (M+), 894, 834, 725, 709, 535, 534, 492, 402, 344, 229, 191, 175, 174.

$UV_{max}^{EtOH}$: 215, 285 nm.

EXAMPLE 4

4''-butyryl-19-deformyltylosin $[(C_6H_5)_3P]_3RhCl$ (200 mg) was added to a solution of 4''-butyryltylosin (200 mg) dissolved in benzene (5 ml) and the mixture was refluxed for six hours. The reaction mixture was filtered and the filtrate was dried in vacuo. The residue was purified by silica gel thin layer chromatography using benzene-acetone (6:1) to yield 4"-butyryl-19-deformyltylosin (133 mg).

TLC: $Rf_A=0.44$.

Mass spectrum (m/e): 957 (M+), 870 (M+-87), 869, 852, 851, 743, 725, 553, 535, 363, 300, 215, 190, 174, 173.

The above 4"-butyryltylosin is prepared by the process disclosed in British Patent Publication No. 2,031,418 A.

Referential Example

4'-demycarosyltylosin

Tylosin (5 g) dissolved in 1 N-HCl (100 ml) was stirred for 22 hours at room temperature. The reaction mixture was adjusted to pH 9 by adding 10% sodium hydroxide and was extracted twice with chloroform (100 ml). The chloroform layer was dehydrated with anhydrous magnesium sulfate and dried in vacuo to obtain crude 4'-demycarosyltylosin (4.4 g) which was purified by silica gel column chromatography using benzene-acetone (1:1) to yield purified product (3.8 g).

TLC: $Rf_A=0.02$, $Rf_B=0.17$.

Mass spectrum (m/e): 771 (M+), 754, 581, 390, 191, 175, 174.

EXAMPLE 5

19-deformyl-4'-demycarosyltylosin

[(C6H5)3P]3RhCl (5.25 g) was added to a solution of 4'-demycarosyltylosin (4 g) dissolved in benzene (100 ml) and the mixture was refluxed for six hours. The reaction mixture was filtered and the filtrate was extracted three times with 1 N-HCl (50 ml). The aqueous layer was adjusted to pH 9 by adding 10% NaOH and extracted twice with chloroform (100 ml). The chloroform layer was dehydrated and dried in vacuo to obtain the crude product (3.2 g) which was purified by silica gel column chromatography using benzene-acetone (1:1) to yield purified 19-deformyl-4'-demycarosyltylosin (1.8 g).

TLC: $Rf_A=0.04$, $Rf_B=0.29$.

Mass spectrum (m/e): 743 (M+), 725, 553, 510, 362, 191, 174.

NMR spectrum (100 MHz, CDCl3): 1.79 (12-CH3), 2.45 [3'-N(CH3)2], 3.45 (2"'-OCH3), 3.61 (3"'-OCH3), disappearance of proton in aldehyde.

UV: $\lambda_{max}^{EtOH}=282.2$ nm ($\epsilon_{max}=22,100$).

EXAMPLE 6

19-deformyl-2,3-didehydro-3-dehydroxy-4'-demycarosyltylosin

Acetic anhydride (5 ml) was added to 19-deformyl-4'-demycarosyltylosin (3 g) dissolved in dry pyridine (10 ml) and the mixture was reacted at 70° C. for 14 hours. The reaction mixture was poured into ice water and adjusted to pH 9.5 by adding 10% NaOH. The precipitate was filtered to obtain crude 3,2',4',4"'-tetraacetyl-19-deformyl-4'-demycarosyltylosin (3.2 g). This was dissolved in methanol (25 ml), 2.8% CH3ONa (5 ml) was added, the mixture was stirred for 1.5 hours at room temperature, acetic acid (0.157 ml) was added and the mixture was refluxed for 20 hours. The reaction mixture was dried in vacuo. Chloroform (100 ml) was added to the residue and the mixture was washed with dilute aqueous ammonia (pH 9). The dehydrated chloroform layer was dried in vacuo. C2H5ONa (675 mg) was added to the residue dissolved in ethanol (30 ml) and the mixture was reacted at 70° C. for 18 hours. The reaction mixture was dried and chloroform (100 ml) was added to the residue, which was then washed with water. The dehydrated chloroform layer was dried to obtain the crude product (2.3 g). The crude substance was purified by silica gel column chromatography using benzene-acetone (2:1) to yield the product (1.5 g).

TLC: $Rf_A=0.06$, $Rf_B=0.32$.

Mass spectrum (m/e): 725 (M+), 707, 535, 344, 191, 175, 174.

NMR spectrum (100 MHz, CDCl3): 1.80 (12-CH3), 2.50 [3'-N(CH3)2], 3.49 (2"'-OCH3), 3.61 (3"'-OCH3).

UV: $\lambda_{max}^{EtOH}=214.5$ nm ($\epsilon=19,800$), 285.2 nm ($\epsilon=19,200$)

EXAMPLE 7

19-deformyl-4'-demycarosyl-23-demysinosyltylosin

4'-demycarosyltylosin (2 g) dissolved in 0.2 N-HCl (12 ml) was adjusted to pH 1.8 by adding 1 N-HCl and the mixture was reacted at 90° C. for 72 hours. The reaction mixture was adjusted to pH 9 by adding 10% NaOH and extracted twice with chloroform (50 ml). The chloroform layer was dehydrated and dried in vacuo to obtain a crude powder (1.5 g) which was dissolved in benzene (15 ml). [(C6H5)3P]3RhCl (2 g) was added and the mixture was refluxed for six hours. The reaction mixture was filtered and the filtrate was extracted twice with 1 N-HCl (50 ml). The aqueous layer was adjusted to pH 9 with 10% NaOH and extracted three times with chloroform (50 ml). The extract was dehydrated and dried in vacuo to obtain the crude powder (1.0 g). The crude powder was purified by silica gel column chromatography using chloroform-methanol (11:1) to elute 19-deformyl-4'-demycarosyltylosin and 19-deformyl-4'-demycarosyl-23-demysinosyltylosin, in this order. Each of the corresponding fractions was collected and dried in vacuo to yield 19-deformyl-4'-demycarosyltylosin (20 mg) and 19-deformyl-4'-demycarosyl-23-demysinosyltylosin (316 mg).

TLC: $Rf_A=0.04$, $Rf_B=0.19$.

Mass spectrum (m/e): 569 (M+), 379 (M+-190), 190, 174, 173.

NMR spectrum (100 MHz, CDCl3): 1.82 (12-CH3), 2.51 [3'-N(CH3)2]

UV: $\lambda_{max}^{EtOH}=283.0$ nm ($\epsilon=20,700$).

EXAMPLE 8

19-deformyl-4'-demycarosyl-3-phenylacetyltylosin

Acetic anhydride (8 ml) was added to 4'-demycarosyltylosin (4 g) dissolved in acetone (20 ml) and the mixture was stirred for three hours at room temperature. The reaction mixture was adjusted to pH 9 with aqueous ammonia and extracted with chloroform (100 ml). The extract was washed with water, dehydrated and dried in vacuo to obtain crude 2',4'-diacetyl-4'-demycarosyltylosin. [TLC: $Rf_A=0.44$, $Rf_B=0.83$] (4.28 g).

Phenylacetylchloride (3. g ml) was added to a solution of the crude material dissolved in dry pyridine (20 ml) and the mixture was stirred at 40° C. for 17 hours. The reaction mixture was poured into cold water (400 ml), adjusted to pH 9.0 with aqueous ammonia and extracted with chloroform (100 ml). The extract was washed with dilute aqueous NaOH, dilute HCl, water and dilute aqueous ammonia and dried in vacuo after dehydration. The residue was dissolved in ammonia saturated with methanol (20 ml), stirred for three hours at room temperature, poured into water (100 ml), then extracted with chloroform (100 ml). The chloroform layer was dehydrated, dried in vacuo and refluxed with methanol (50 ml) for 17 hours.

After checking the removal of the protective group at positions -2' and -4' by TLC, the reaction mixture was dried in vacuo, dissolved in benzene (70 ml) and washed once with water. The benzene layer was dehydrated with anhydrous magnesium sulfate and [(C$_6$H$_5$)$_3$P]$_3$RhCl (3.6 g) was added thereto, and the mixture was heated at 80° C. for six hours. The filtrate was extracted three times with 1 N HCl (100 ml). The extract was neutralized with 10% aqueous NaOH to adjust the pH to 9.0, and extracted three times with chloroform (100 ml). The chloroform layer was dehydrated, and dried in vacuo. The residue was purified by silica gel column chromatography using chloroform-methanol (20:1) to yield the product (404 mg).

TLC: Rf$_B$=0.37.

Mass spectrum (m/e): 861 (M+), 725, 535, 190, 175, 174, 173.

NMR spectrum (100 MHz, CDCl$_3$): 1.79 (12-CH$_3$), 2.50 [3'-N(CH$_3$)$_2$], 3.45 (2'''-OCH$_3$), 3.60 (3'''-OCH$_3$, —CH$_2$-ph), 7.26 (ph).

IR (KBr tablet): 1596 cm$^{-1}$ (ph).

EXAMPLE 9

3,4'''-diacetyl-19-deformyl-4'-demycarosyltylosin 3,2',4',4'''-tetraacetyl-19-deformyl-4'-demycarosyltylosin (100 mg) obtained in Example 5 dissolved in methanol (10 ml) was refluxed for 16 hours. The reaction mixture was dried in vacuo and the residue was purified by alumina column chromatography using benzene-ethyl acetate (1:1) to obtain the product (82.7 mg).

TLC: Rf$_B$=0.37.

Mass spectrum (m/e): 827 (M+), 767, 594, 535, 345, 344, 217, 190, 174, 173.

NME spectrum (100 MHz, CDCl$_3$): 2.06 (3-OAc), 2.11 (4'''-OAc), 2.49 [3'-N(CH$_3$)$_2$], 3.44 (2'''-OCH$_3$), 3.51 (3'''-OCH$_3$).

EXAMPLE 10

3-acetyl-19-deformyl-4'-demycarosyltylosin

In Example 7, phenylacetylchloride (6.3 ml) was replaced by acetylchloride (1.84 ml) to produce the product (362 mg).

TLC: Rf$_B$=0.27.

Mass spectrum (m/e): 785 (M+), 725, 535, 421, 405, 362, 345, 344, 190, 174, 173.

EXAMPLE 11

19-deformyl-4'-demycarosyl-3-propionyltylosin

In Example 7, phenylacetylchloride (6.3 ml) was replaced by propionylchloride (2.25 ml) to produce the product (412 mg).

TLC: Rf$_B$=0.31.

Mass spectrum (m/e): 799 (M+), 725, 535, 435, 419, 362, 345, 344, 190, 174, 173.

EXAMPLE 12

3-butyryl-19-deformyl-4'-demycarosyltylosin

In Example 7, phenylacetylchloride (6.3 ml) was replaced by butyrylchloride (2.69 ml) to produce the product (523 mg).

TLC: Rf$_B$=0.33.

Mass spectrum (m/e): 813 (M+), 725, 535, 449, 433, 362, 345, 344, 190, 174, 173.

EXAMPLE 13

4'''-butyryl-19-deformyl-4'-demycarosyltylosin

Dry pyridine (0.26 ml) was added to a solution of 2',4'-diacetyl-4'-demycarosyltylosin (1.28 g) obtained in Example 7 dissolved in dry dichloromethane (10 ml), butyrylchloride (0.31 ml) was added and the mixture was stirred for one hour at room temperature. Chloroform (20 ml) was added to the reaction mixture. The aqueous layer was adjusted to pH 9 by adding aqueous ammonia and shaken to extract. The chloroform layer was washed with diluted HCl, water and diluted NaOH, dehydrated and dried in vacuo. The residue was dissolved in methanol (20 ml), refluxed for 16 hours and dried in vacuo. The residue was dissolved in chloroform (20 ml), washed with dilute aqueous NaOH and water, dehydrated, and dried in vacuo. The residue was dissolved in benzene (25 ml), [(C$_6$H$_5$)$_3$P]$_3$RhCl (1.3 g) was added and the mixture was heated at 80° C. for six hours. The reaction mixture was filtered, and the filtrate was dried in vacuo to obtain the crude product, which was purified by silica gel column chromatography using chloroform-methanol (20:1) to produce the purified product (620 mg).

TLC: Rf$_B$=0.37.

Mass spectrum (m/e): 813 (M+), 640, 623, 622, 568, 553, 552, 362, 245, 190, 174, 173.

NMR spectrum (100 MHz, CDCl$_3$): 2.49 [3'-N(CH$_3$)$_2$], 3.46 (2'''-OCH$_3$), 3.51 (3'''-OCH$_3$).

EXAMPLE 14

19-deformyl-10, 11, 12, 13-tetrahydro-3-dehydroxy-4'-demycarosyltylosin 19-deformyl-2,3-didehydro-3-dehydroxy-4'-demycarosyltylosin (100 mg) obtained in Example 5 was dissolved in methanol (4 ml). 5% Pd-carbon catalyst (50 mg) was added therein and starting material was subjected to catalytic reduction for eight hours at room temperature. The reaction mixture was filtered to remove the catalyst and the filtrate was dried in vacuo to produce the product (85 mg).

TLC: Rf$_B$=0.31.

Mass spectrum (m/e): 731 (M+), 541 (M+-191), 350, 191, 175, 174.

UV: no absorption.

EXAMPLE 15

19-deformyl-10, 11, 12, 13-tetrahydro-4'-demycarosyltylosin:

19-deformyl-4'-demycarosyltylosin (100 mg) obtained in Example 4 was dissolved in ethanol (5 ml). 5% Pd-carbon catalyst (50 mg) was added therein, and the starting material was subjected to catalytic reduction for six hours at room temperature. The reaction mixture was filtered to remove the catalyst, and the filtrate was dried in vacuo to yield the product (90 mg).

TLC: Rf$_B$=0.02.

Mass spectrum (m/e): 747 (M+), 557 (M+-191), 366, 191, 175, 174.

UV: no absorption.

EXAMPLE 16

20-deoxo-4'-demycarosyltylosin

Tylosin (5 g) was dissolved in a mixture (150 ml) of 0.2 M phosphate buffer (pH 7.5 )-methanol (1:1), NaBH$_4$ (150 mg) dissolved in the same mixture (10 ml)

was added thereto, the reaction mixture was stirred for 1.5 hours at room temperature, adjusted to pH 9.5 by adding dilute aqueous ammonia, and then the reaction mixture was extracted with chloroform (100 ml). The chloroform layer was washed with water, dehydrated with anhydrous magnesium sulfate and dried in vacuo to obtain a crude 20-dihydrotylosin [UV: $\lambda_{max}\cdot^{EtOH}$=283 nm, $Rf_B$=0.15].

The crude product was dissolved in pyridine (20 ml). Tosylchloride (1.25 g) was added thereto, and the mixture was stirred for 16 hours at room temperature. Concentrated ammonia (5 ml) was added to the reaction mixture, which was stirred for 15 minutes, poured into water (500 ml) and extracted with chloroform (100 ml). The chloroform layer was washed with water, dilute HCl, water and dilute aqueous ammonia, in this order, dehydrated with anhydrous magnesium sulfate and dried in vacuo. The thus-obtained powder (3.3 g) was dissolved in ethylene glycol-dimethyl ether (30 ml). Sodium iodide (2.3 g) and zinc powder (2 g) were added thereto and the mixture was refluxed for three hours. The reaction mixture was filtered to remove zinc powder. Water (100 ml) was added to the filtrate, which was then adjusted to pH 9.5 by adding dilute ammonia and extracted with chloroform (100 ml). The chloroform layer was washed with water, dehydrated with magnesium sulfate and dried in vacuo to obtain crude 20-deoxo-4'-demycarosyltylosin ($Rf_B$=0.24).

The crude product dissolved in 0.5 N HCl (50 ml) was stirred for 18 hours at room temperature. The reaction mixture was adjusted to pH 9.5 with aqueous ammonia and extracted with chloroform (100 ml). The chloroform layer was washed with water, dehydrated with magnesium sulfate and dried in vacuo to obtain a crude powder (2.2 g) of 20-deoxo-4'-demycarosyltylosin. The powder was purified by silica gel column chromatography using chloroform-methanol (15:1) to yield the purified product (780 mg).

TLC: $Rf_B$=0.32.

UV: $\lambda_{max}^{EtOH}$=283 nm ($\epsilon$=19,700).

Mass spectrum (m/e): 757 (M+), 739, 612, 567, 394, 393, 377, 359, 358, 190, 174, 173.

NMR spectrum (100 MHz, CDCl$_3$): 1.79 (12-CH$_3$), 2.51 [3'-N(CH$_3$)$_2$], 3.42 and 3.49 (OCH$_3$), disappearance of aldehyde peak.

What is claimed is:

1. A compound of the formula

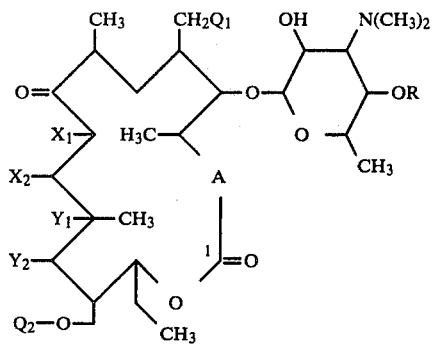

wherein A is

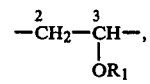

—CH=CH— or —CH$_2$—CH$_2$—, R$_1$ is hydrogen, lower alkanoyl or phenyl-lower alkanoyl, X$_1$ and X$_2$ are hydrogen or are connected to form a valence bond, Y$_1$ and Y$_2$ are hydrogen or are connected to form a valence bond, Q$_1$ is hydrogen or methyl, Q$_2$ is hydrogen or

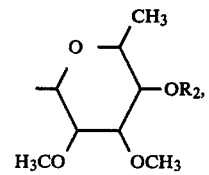

R$_2$ is hydrogen or lower alkanoyl, R is hydrogen or

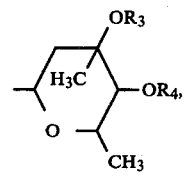

R$_3$ is hydrogen or C$_{2-5}$ alkanoyl, and R$_4$ is hydrogen or C$_{2-6}$ alkanoyl, and when R$_3$ is not hydrogen, then R$_4$ is not hydrogen, or a pharmaceutically acceptable salt thereof.

2. A compound as claimed in claim 1, wherein said compound is 19-deformyltylosin or a pharmaceutically acceptable salt thereof.

3. A compound of the formula

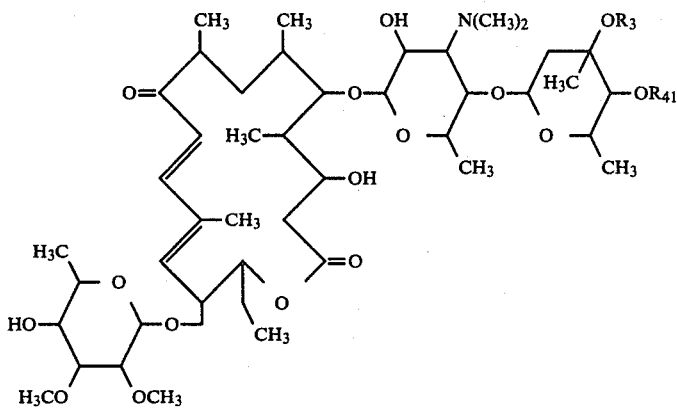

wherein $R_3$ is hydrogen or $C_{2-5}$ alkanoyl, and $R_{41}$ is $C_{2-6}$ alkanoyl, or a pharmaceutically acceptable salt thereof.

4. A compound as claimed in claim 3, wherein $R_3$ is hydrogen.

5. A compound as claimed in claim 3, wherein $R_3$ is $C_{2-5}$ alkanoyl.

6. A compound as claimed in claim 5, wherein said compound is 3''-acetyl-19-deformyl-4''-isovaleryltylosin or a pharmaceutically acceptable salt thereof.

7. A compound of the formula

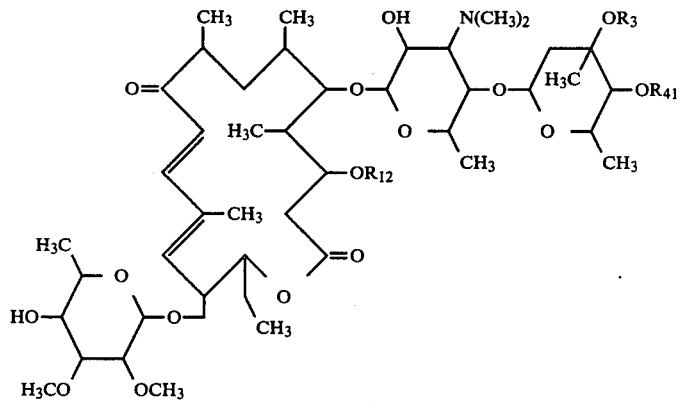

wherein $R_{12}$ is lower alkanoyl, $R_3$ is hydrogen or $C_{2-5}$ alkanoyl and $R_{41}$ is $C_{2-6}$ alkanoyl, or a pharmaceutically acceptable salt thereof.

8. A compound as claimed in claim 7, wherein said compound is 3,3'',4''-triacetyl-19-deformyltylosin, or a pharmaceutically acceptable salt thereof.

9. A compound as claimed in claim 1, wherein said compound is represented by the formula

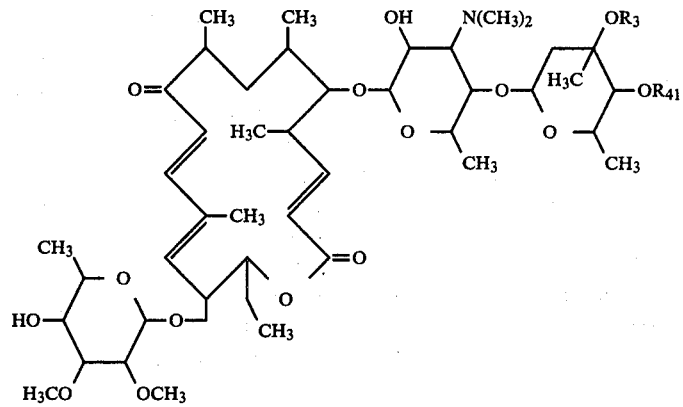

wherein $R_3$ is hydrogen or $C_{2-5}$ alkanoyl and $R_{41}$ is $C_{2-6}$ alkanoyl, or a pharmaceutically acceptable salt thereof.

10. A compound as claimed in claim 9, wherein said compound is 3'', 4''-diacetyl-19-deformyl-2,3-didehydro-3-dehydroxytylosin or a pharmaceutically acceptable salt thereof.

11. A compound as claimed in claim 1, wherein said compound is represented by the formula

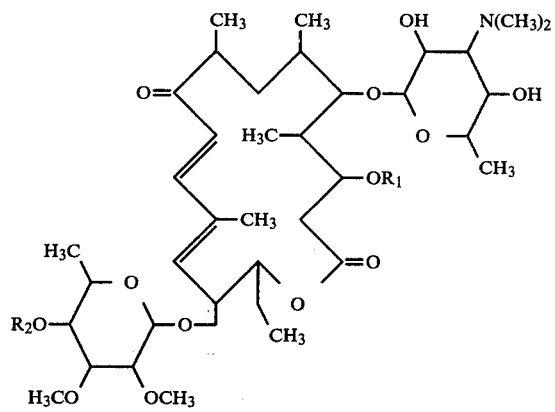

wherein $R_1$ is hydrogen, lower alkanoyl or phenyl-lower alkanoyl and $R_2$ is hydrogen or lower alkanoyl, or a pharmaceutically acceptable salt thereof.

12. A compound as claimed in claim 11, wherein said compound is 19-deformyl-4'-demycarosyltylosin or a pharmaceutically acceptable salt thereof.

13. A compound as claimed in claim 11, wherein $R_1$ is lower alkanoyl and $R_2$ is hydrogen, or a pharmaceutically acceptable salt thereof.

14. A compound as claimed in claim 13, wherein said compound is 3-acetyl-19-deformyl-4'-demycarosyltylosin or a pharmaceutically acceptable salt thereof.

15. A compound as claimed in claim 13, wherein said compound is 19-deformyl-4'-demycarosyl-3-propionyltylosin or a pharmaceutically acceptable salt thereof.

16. A compound as claimed in claim 13, wherein said compound is 3-butyryl-19-deformyl-4'-demycarosyltylosin or a pharmaceutically acceptable salt thereof.

17. A compound as claimed in claim 11, wherein $R_1$ is phenyl-lower alkanoyl and $R_2$ is hydrogen or a pharmaceutically acceptable salt thereof.

18. A compound as claimed in claim 17, wherein said compound is 19-deformyl-4'-demycarosyl-3-phenylacetyltylosin or a pharmaceutically acceptable salt thereof.

19. A compound as claimed in claim 11, wherein $R_1$ is hydrogen and $R_2$ is lower alkanoyl, or a pharmaceutically acceptable salt thereof.

20. A compound as claimed in claim 19, in which said compound is 4'''-butyryl-19-deformyl-4'-demycarosyltylosin or a pharmaceutically acceptable salt thereof.

21. A compound as claimed in claim 11, wherein $R_1$ and $R_2$ are lower alkanoyl.

22. A compound as claimed in claim 21, wherein said compound is 3,4'''-diacetyl-19-deformyl-4'-demycarosyltylosin or a pharmaceutically acceptable salt thereof.

23. A compound as claimed in claim 1, wherein said compound is 19-deformyl-2,3-didehydro-3-dehydroxy-4'-demyarosyltylosin or a pharmaceutically acceptable salt thereof.

24. A compound as claimed in claim 1, wherein said compound is 19-deformyl-4'-demycarosyl-10,11,12,13-tetrahydrotylosin or a pharmaceutically acceptable salt thereof.

25. A compound as claimed in claim 1, wherein said compound is 19-deformyl-3-dehydroxy-4'-demycarosyl-10,11,12,13-tetrahydrotylosin or a pharmaceutically acceptable salt thereof.

26. A compound as claimed in claim 1, wherein said compound is 19-deformyl-4'-demycarosyl-23-demysinosyltylosin or a pharmaceutically acceptable salt thereof.

27. A compound as claimed in claim 1, wherein said compound is 20-deoxo-4'-demycarosyltylosin or a pharmaceutically acceptable salt thereof.

* * * * *